(12) United States Patent
Gazzoli (10) Patent No.: US 6,443,057 B1
(45) Date of Patent: Sep. 3, 2002

(54) DOMESTIC WASTE TREATMENT SYSTEM

(76) Inventor: Renzo Gazzoli, Via G. Garibaldi, 28, 46020 Pegognaga (IT)

( * ) Notice: Subject to any disclaimer, the term of this patent is extended or adjusted under 35 U.S.C. 154(b) by 0 days.

(21) Appl. No.: 09/564,697

(22) Filed: May 4, 2000

(30) Foreign Application Priority Data

May 7, 1999 (IT) ........................................ MN99A0020

(51) Int. Cl.$^7$ .................................................. B30B 1/32
(52) U.S. Cl. ..................... 100/225; 100/269.17; 100/99
(58) Field of Search ............................ 100/100, 52, 99, 100/225, 269.17

(56) References Cited

U.S. PATENT DOCUMENTS

| | | | | |
|---|---|---|---|---|
| 3,995,543 A | * | 12/1976 | Montalbano | 100/229 A |
| 4,095,519 A | * | 6/1978 | Budoff | 100/35 |
| 5,111,927 A | * | 5/1992 | Schulze, Jr. | 100/902 |
| 5,129,318 A | * | 7/1992 | Zimmer | 100/102 |
| 5,143,246 A | * | 9/1992 | Johnson et al. | 220/23.83 |
| 5,167,184 A | * | 12/1992 | Rebecchi | 100/131 |
| 5,172,630 A | * | 12/1992 | Thompson | 100/193 |
| 5,205,698 A | * | 4/1993 | Mezey | 414/406 |
| 5,259,304 A | * | 11/1993 | Roberts | 100/215 |
| 5,425,458 A | * | 6/1995 | Gilcreest et al. | 100/45 |
| 5,478,186 A | | 12/1995 | Zuidema | |
| 5,490,455 A | * | 2/1996 | Conti et al. | 100/100 |
| 5,813,323 A | * | 9/1998 | Nowak | 100/223 |

FOREIGN PATENT DOCUMENTS

| | | |
|---|---|---|
| DE | 40 01 768 | 7/1991 |
| DE | 93 15 201 | 2/1994 |

* cited by examiner

Primary Examiner—Allen Ostrager
Assistant Examiner—William Hong
(74) Attorney, Agent, or Firm—Guido Modiano; Albert Josif; Daniel O'Byrne (57) ABSTRACT

A domestic waste treatment system, comprising: a compaction and disposal device; a curbside bin, which is adapted to receive the waste, contained in a tray provided with an openable bottom and divided according to type in the compartments of the tray; a truck which is adapted to receive the waste, contained in a bin provided with an openable bottom and divided according to type in the compartments of the bin; a final treatment plant, which is adapted to receive the waste, contained in a container provided with an openable bottom and divided according to type in the compartments of the container.

31 Claims, 10 Drawing Sheets

DOMESTIC WASTE TREATMENT SYSTEM

BACKGROUND OF THE INVENTION

The invention relates to a domestic waste treatment system.

The many problems linked to the presence of the waste generated daily in domestic environments are well-known. Among them, the volume of the waste, which is increasingly difficult to control, and the now compulsory need to provide for sorted collection by separating said waste according to types designed for different processes in final treatment plants, are particularly pressing issues.

SUMMARY OF THE INVENTION

The aim of the present invention is to provide a domestic waste treatment system, which by using a global approach to deal with all the problems is capable of ensuring optimum functionality.

The proposed aim is achieved by a domestic waste treatment system according to the invention, characterized in that it consists of a compaction and disposal device which comprises:

- a plurality of compaction chambers, which are arranged so as to receive different types of waste introduced through individual loading openings, and which are provided with at least one plate actuated by actuation means and adapted to act on said waste so as to reduce its volume:
- at least one additional compartment designed for disposal of organic waste;
- a pull-out tray arranged below the compaction chambers and provided with partitions which form a plurality of compartments which are adapted to receive, by gravity, the different types of waste contained at least in said compaction chambers so as to keep them separated, said tray being provided with an openable bottom and with means suitable to receive a lid;
- a lid which is as sociable with the pull-out tray;
- a pull-out divider which is arranged at the base of the plurality of compaction chambers.

The domestic waste treatment system according to the invention further comprises a curbside bin which is suitable to receive said waste contained in a tray provided with an openable bottom, said waste being divided according to type in the several compartments of said tray, said bin comprising:

- resting means for resting on the road paving;
- gripping means for being gripped by a waste transport truck;
- an openable bottom;
- an opening formed in a wall in an elevated position proximate to the lid, suitable to allow the complete insertion of said tray in said bin;
- a plurality of walls which are adapted to divide the internal space of the bin into compartments which extend from the bottom and end upward at openings which are arranged so that there is one of said openings below each one of the compartments provided in said tray when said tray is fully inserted in the bin.

The system according to the invention further comprises a truck which is adapted to receive the waste contained in a bin provided with an openable bottom, said waste being divided according to type in the several compartments with which said bin is provided, said truck comprising:

- a container which can be removed from the truck that carries it and is provided with an opening formed in the lid and with a plurality of walls which are adapted to divide the internal space into compartments which extend from the bottom and end upward in said opening at openings which are located so that there is one below each one of the compartments provided in said bin when said bin is arranged above said opening, said container being provided with an openable bottom;
- handling means for handling the bin, which are adapted to move said bin from the position in which it rests on the road paving to a position in which it lies above said opening provided within the lid of the container;
- handling means for handling the openable bottom of the bin, adapted to discharge the waste contained in the several compartments of the bin into the corresponding openings which end at said opening provided in the lid of the container.

Finally, the domestic waste treatment system according to the invention comprises a final treatment plant which is adapted to receive waste which is contained in a container provided with an openable bottom and is divided according to type in the several compartments of said container, said plant comprising:

- lifting means adapted to lift the container from the platform of the transport truck to a position which lies above inlets of channels arranged so that there is one inlet below each one of the compartments provided in said container, said channels being such as to convey the different types of waste received by gravity from the container to the points for treating said individual types of waste;
- handling means adapted to handle the bottom of the container.

BRIEF DESCRIPTION OF THE DRAWINGS

Further characteristics and advantages of the present invention will become better apparent from the following detailed description of a few preferred but not exclusive embodiments thereof, illustrated only by way of non-limitative example in the accompanying drawings, wherein.

DESCRIPTION OF THE PREFERRED EMBODIMENTS

With reference to the above FIGS. 1 to 4, 1 designates a basic module of the compaction and disposal device, and the reference numeral 2 designates the outline of a module which can be associated with said basic module and is described hereinafter.

Figure 1:
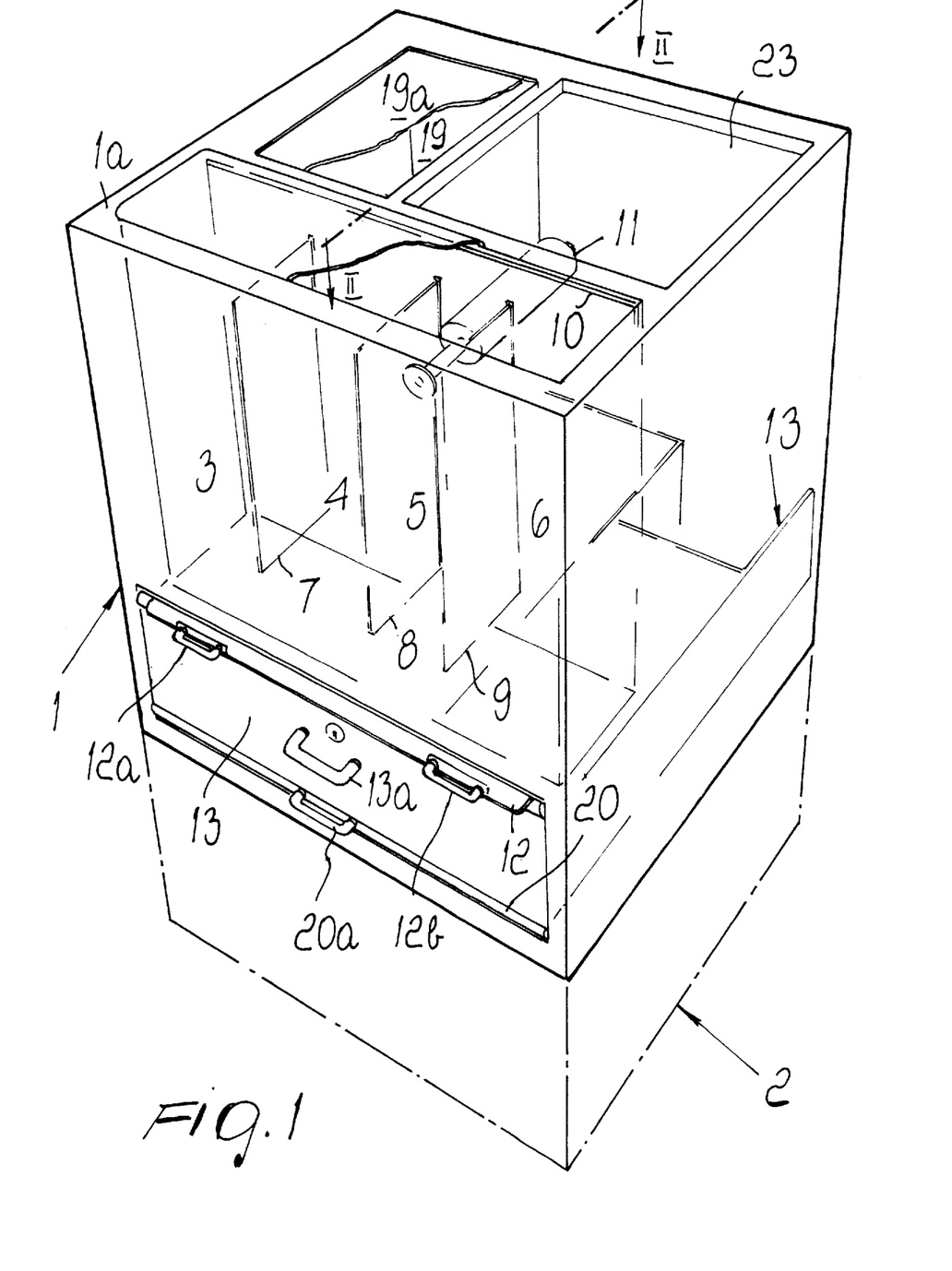
FIG. 1 is a perspective view with parts, shown in phantom lines, of the basic module, and of an additional associated module shown in dot-and-dash lines.
Figure 2:
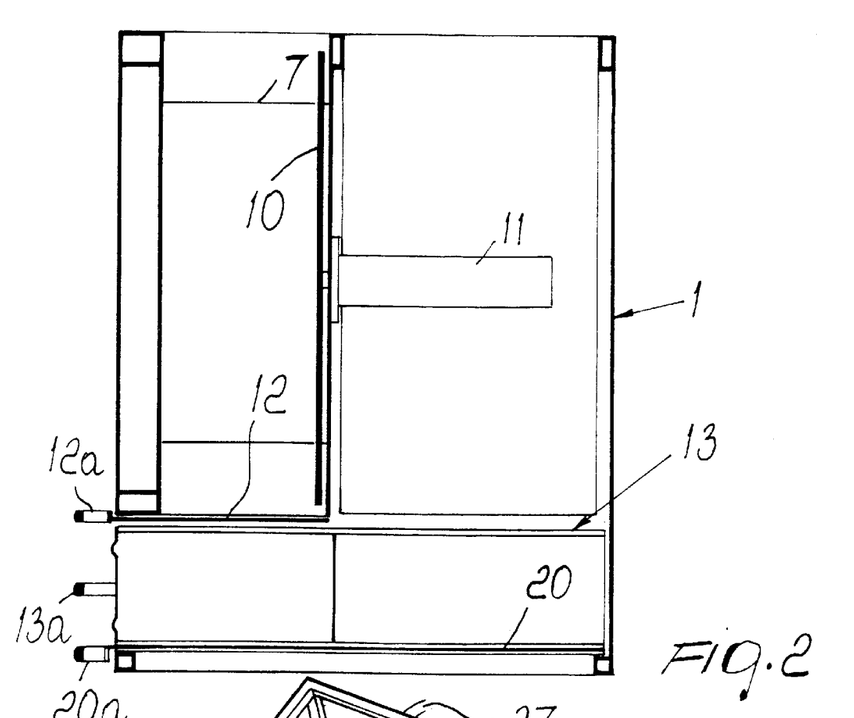
FIG. 2 is a sectional view, taken along the plane II—II of FIG. 1.

Said basic module 1 comprises a plurality of compaction chambers, designated by the reference numerals 3, 4, 5 and 6 respectively, which are delimited by the outside walls of the module and by the partitions 7, 8 and 9, and are arranged so as to receive different materials which are introduced through individual loading openings located at the lid 1a of the module; merely by way of example, it is assumed that the chamber 3 receives glass objects, the chamber 4 receives objects made of metals other than aluminum, the chamber 5 receives aluminum objects such as ordinary beverage cans, and the chamber 6 receives plastic objects.

Figure 4:
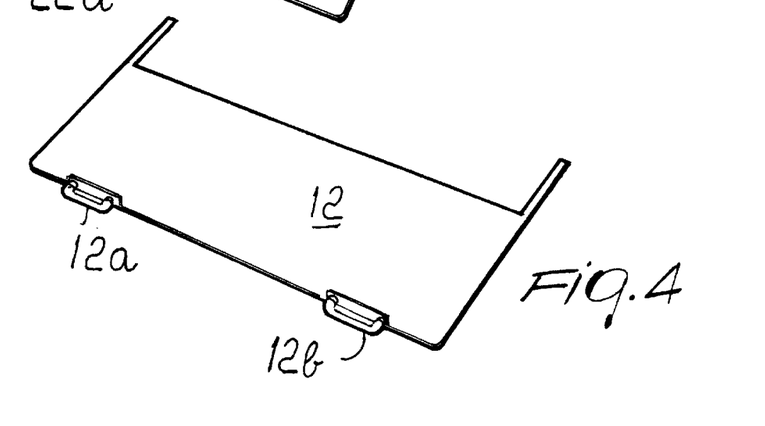
FIG. 4 is a view of the removable divider.

Said chambers are provided with the plate 10, which has slots for the passage of the partitions 7, 8 and 9 and is actuated by the actuation cylinder 11 in order to act on the waste contained in the chambers 3, 4, 5, 6 so as to reduce its volume; moreover, said chambers are delimited at the bottom by the pull-out divider 12 provided with handles 12a, 12b.

One or more of the compaction chambers may be provided with a cutter for breaking up the material that is introduced, comprising a blade and a contrast blade which are respectively fixed to the plate 10 and to the wall of the module that lies opposite thereto.

Figure 3:
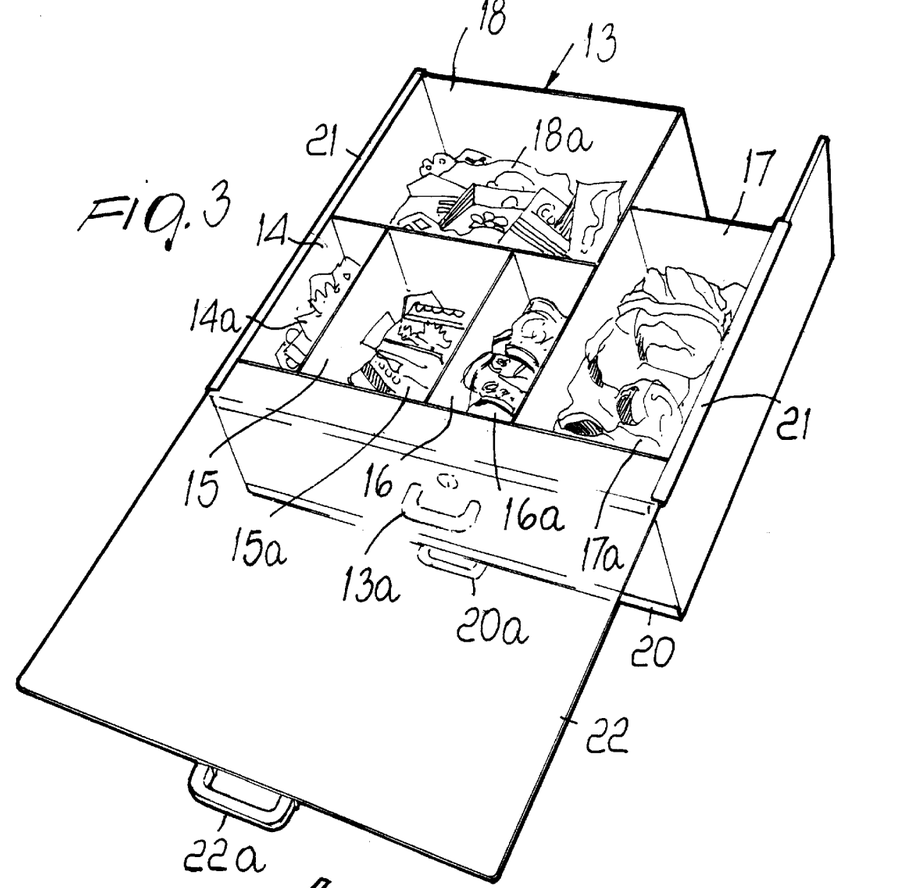
FIG. 3 is a view of the tray, pulled out of the basic module and provided with the corresponding lid.

At the base of the module 1 there is provided the pull-out tray, generally designated by the reference numeral 13, which is provided with a handle 13a and with partitions which first of all form compartments which are suitable to receive, by gravity, the waste contained in the compaction chambers so as to keep it sorted; accordingly, the compartment 14 is arranged so as to receive objects made of glass 14a from the chamber 3, the compartment 15 receives objects 15a made of metal except aluminum from the chamber 4, the compartment 16 receives objects 16a made of aluminum from the chamber 5, and the compartment 17 receives plastic objects 17a from the chamber 6.

The tray 13 also comprises the compartment 18, which is designed to receive a material which does not require compaction, such as for example paper 18a, and which reaches it directly by gravity by means of the chute 19 with a loading opening which is located at the lid 1a of the module and is protected by the lid 19a.

The tray is provided with a bottom 20 which can open by sliding and has 20a handle 20a, and with guides 21 suitable to receive the sliding lid 22 with a handle 22a.

The basic module 1 is complete by the presence of the compartment 23 designed to dispose of organic waste, as explained in greater detail hereinafter; said compartment is not connected to the tray 13.

Before ending the description of the basic module 1 of the compaction and disposal device, it should be observed that the number of compaction chambers comprised therein may be any, and that said chambers may obviously be designed for any material and may have one or more plates actuated in any manner; there may also be more than one chute such as 19 which is directly connected to a corresponding compartment formed in the underlying tray, but said chute may also be omitted.

It is also possible to provide for additional portions of space which are open exclusively at the loading opening, also acting as discharge opening, for containing particular waste.

It should also be observed that the bottom of the tray 13 may be openable in any manner, and that the lid of the tray may be associated therewith in any manner.

Figure 5:
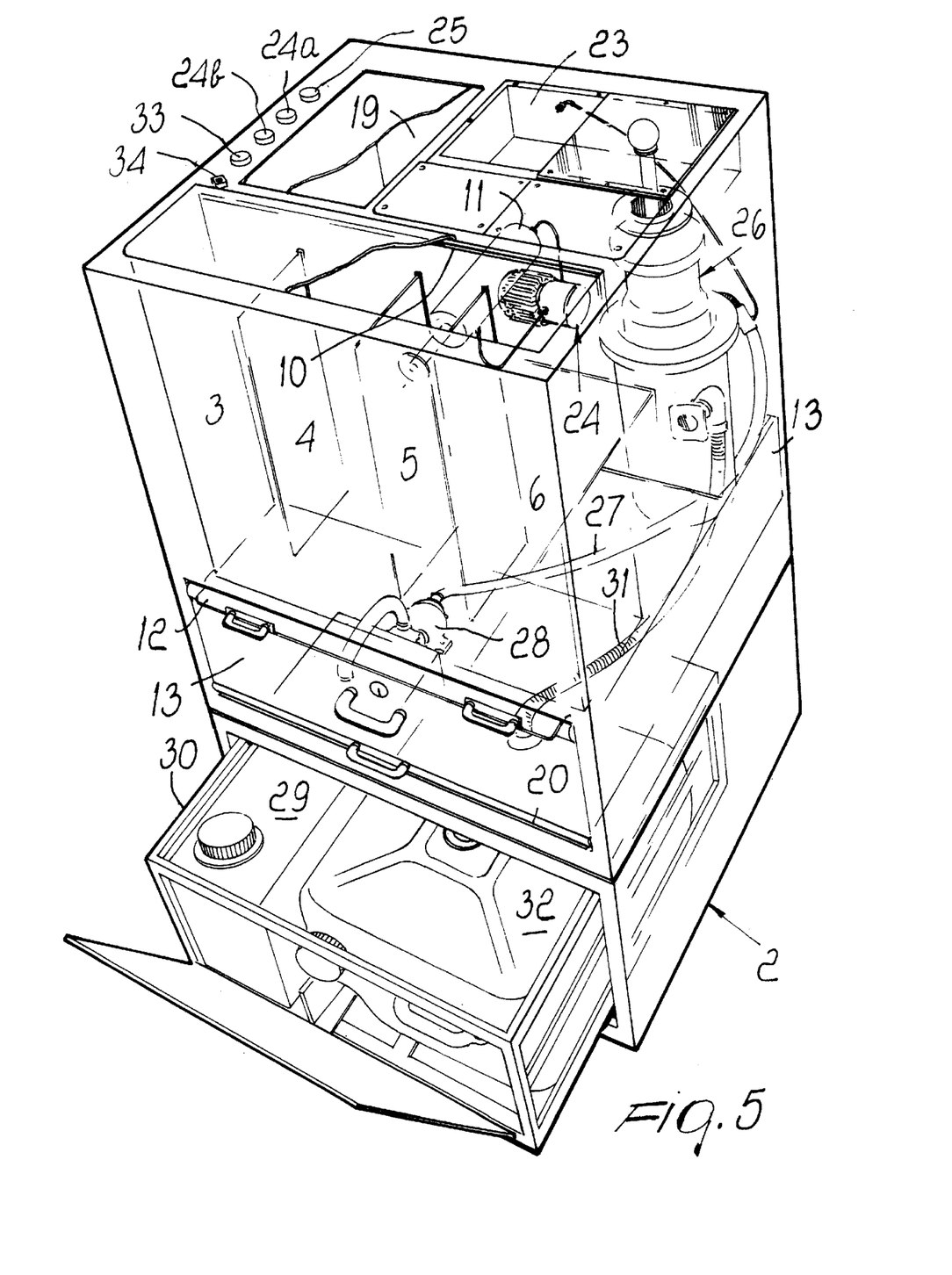
FIG. 5 is a view of the compaction and disposal device according to a first embodiment.

A first embodiment of the compaction and disposal device according to the invention is shown in FIG. 5 and is achieved by providing the basic module with the additions that are now described.

First of all it, there is a drive 24 for the actuation cylinder 11, which is provided with an electric pump operated by means of the pushbuttons 24a, 24b, contiguous to the master switch 25.

Moreover, the compartment 23 accommodates the conventional disposer 26, which reduces to pulp the organic residues, such as peel and kitchen waste, dropped into said compartment 23.

The water required for the operation of the disposer is supplied by means of the duct 27 by the pump 28, drawing it from the reservoir 29 contained in the structure 30 which can be pulled out of the module 2 associated with the basic module converted as described.

The pulp produced by the disposer is conveyed, by means of the duct 31, to the container 32, which is accommodated in the structure 30 so that it can be moved away for periodic emptying.

The reference numeral 33 designates the pushbutton for actuating the disposer 26 and the pump 28, and the reference numeral 34 designates the luminous warning for indicating the presence of water in the reservoir 29.

The operation of the device is evident.

The user introduces the different types of waste as abovedescribed in the compaction and disposal device in the active configuration, in which the divider 12 is inserted at the base of the compaction chambers 3, 4, 5, 6 and the tray 13 is inserted without the lid 22 and with the bottom 20; clearly, the disposer 26 is operated every time organic substances are introduced in the compartment 23, and water is periodically topped up in the reservoir 29 and the pulp container 32 is periodically emptied.

When the waste introduced in the compaction chambers reaches a set level, the plate 10 is actuated, compressing said waste and considerably reducing its volume; at this point the divider 12 is pulled out, and the compacted waste accordingly falls into the several compartments of the tray 13, which when deemed appropriate is pulled out, provided with the lid 22, and carried for emptying to a curbside bin as described hereinafter.

Figure 6:
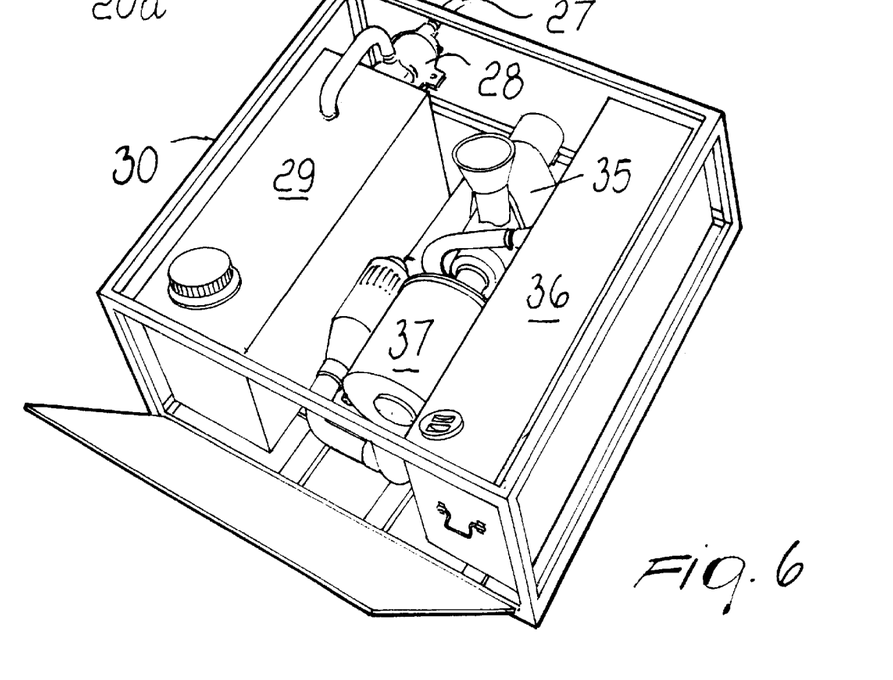
FIG. 6 is a view showing a different form of a detail of the embodiment of FIG. 5.

FIG. 6 shows a different form of the elements contained in the structure 30 that can be pulled out of the module 2 associated with the basic module.

According to this different form, means for compacting the pulp produced by the disposer 26 are associated with the reservoir 29 for the water that is sent to said disposer by the pump 28 by means of the duct 27; said means comprise the separator 35 for separating the liquid fraction that reaches the reservoir 36 from the solid fraction that reaches the dryer 37 and can be removed as powder or granules.

Anyhow the solid fraction of the pulp may be compacted by virtue of any means.

Figure 7:
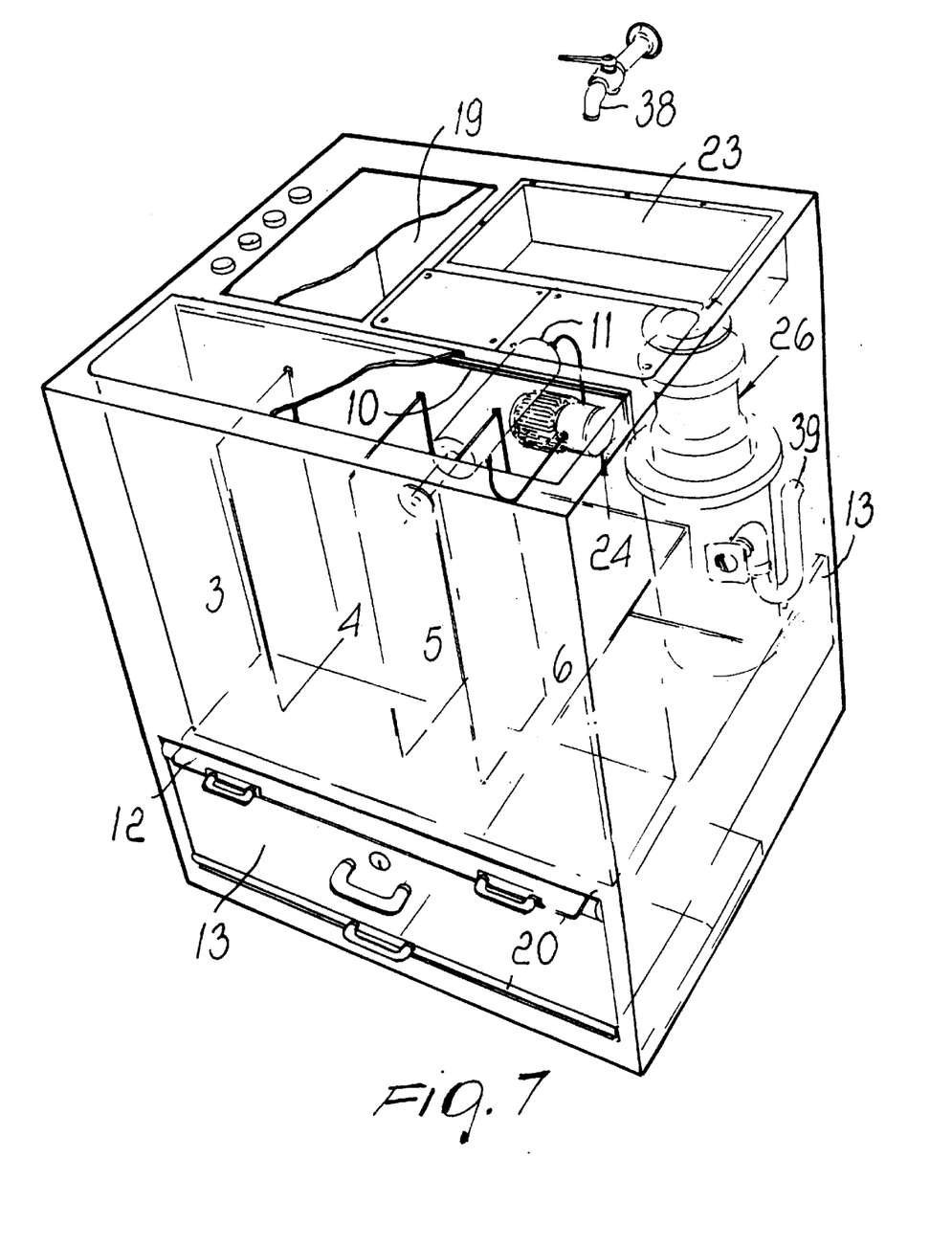
FIGS. 7 and 8 are views of additional embodiments of the compaction and disposal device.

A different embodiment of the compaction and disposal device is shown in FIG. 7: in this embodiment, the basic module has again been integrated with the drive 24, which is provided with an electric pump, and with the disposer 26; however, differently from what occurs in the previously described embodiment, said disposer receives the water required for operation from the tap 38 and discharges the resulting pulp into the domestic sewage system by means of the duct 39.

Figure 8:
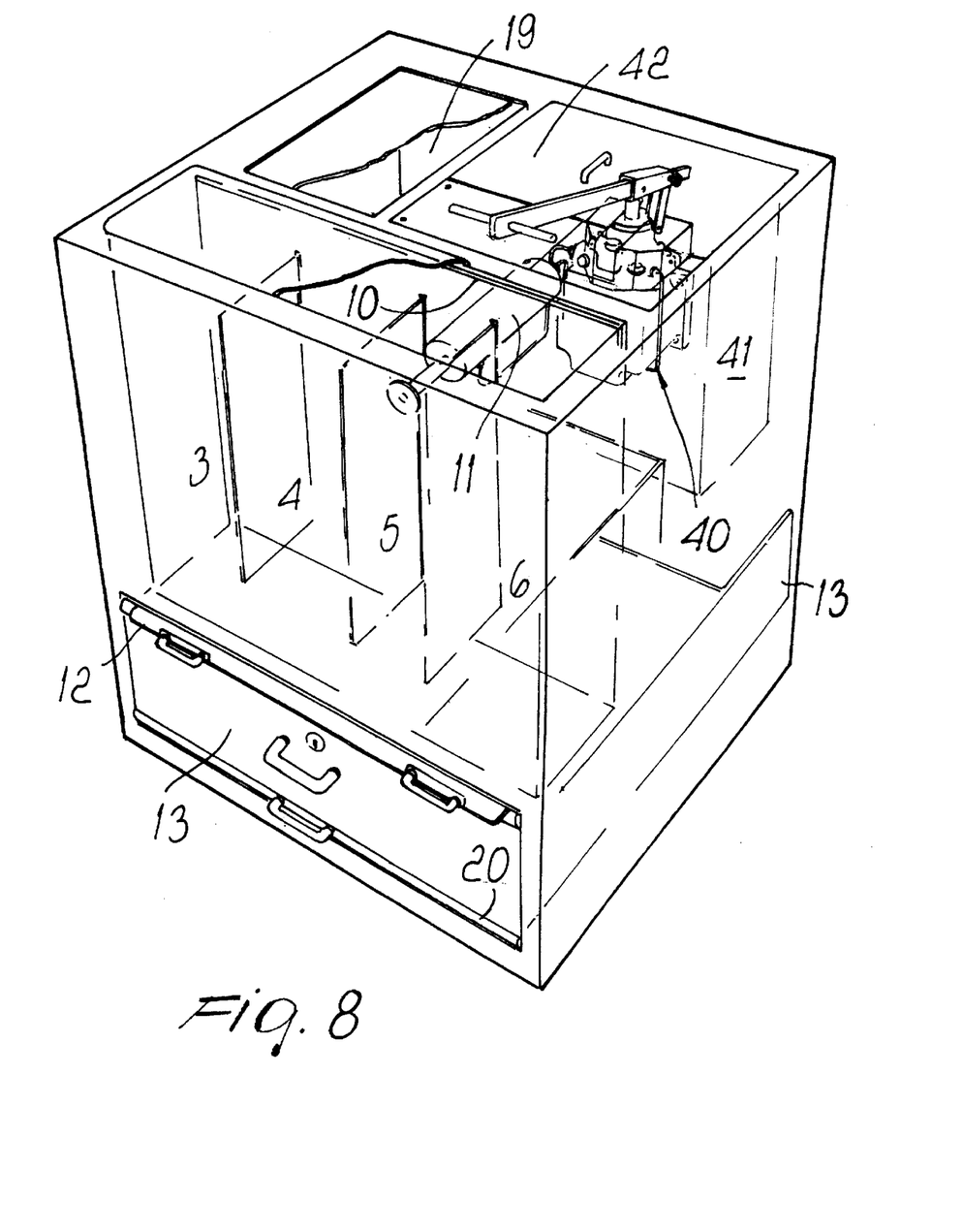

In the further embodiment shown in FIG. 8, the basic module has been integrated by simply adding the manual drive 40 for actuating the actuation cylinder 11 and the simple container 41, which is protected by the lid 42 and is suitable to contain organic substances which are periodically emptied.

Other embodiments of the compaction and disposal device are of course possible, for example by combining the presence of the disposer 26 with a manual drive for actuating the actuation cylinder 11; all said embodiments are suitable to be inserted within kitchen units and the like or in any case in small spaces which are easily available in homes.

Figures 9, 10:
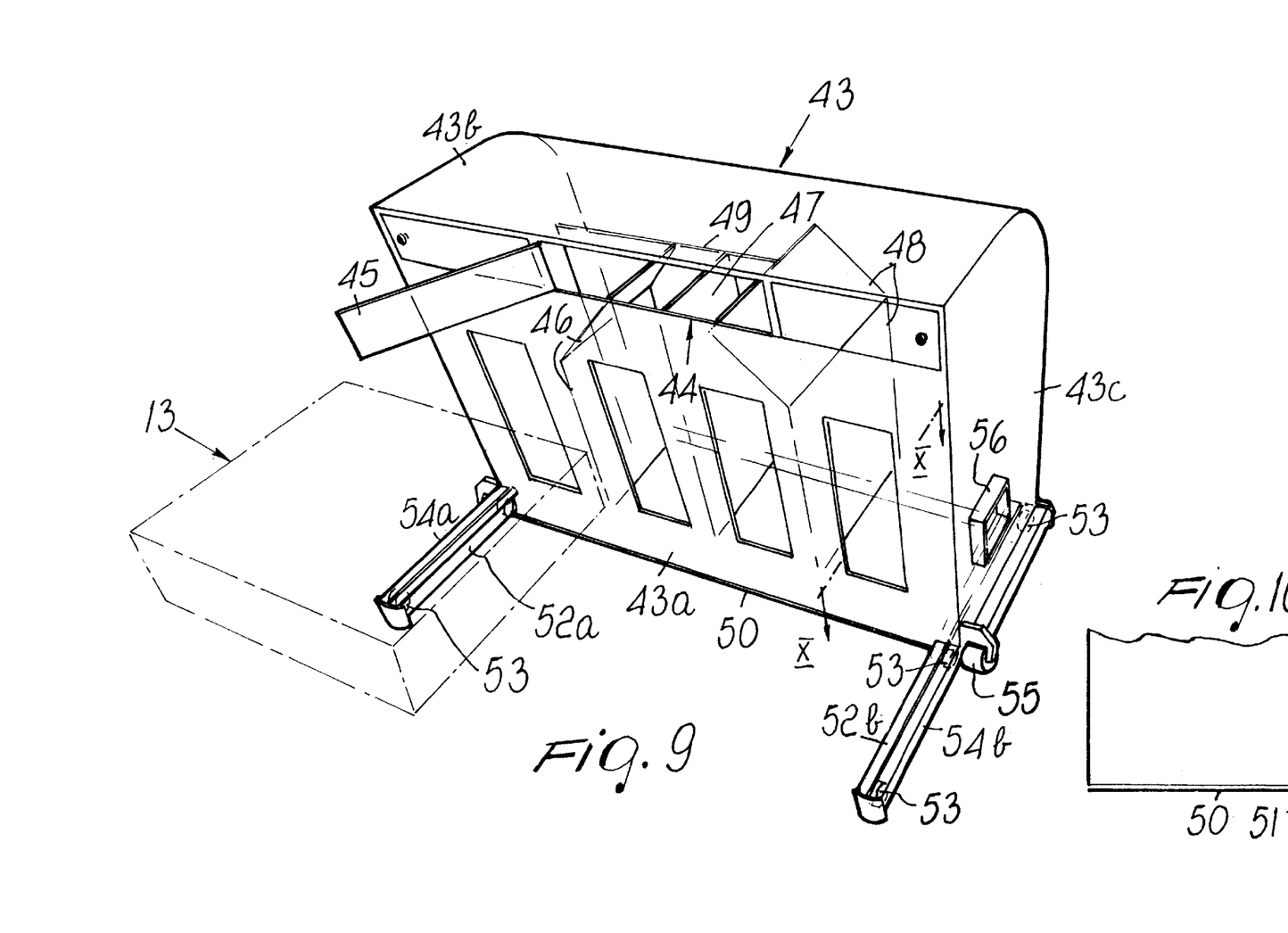
FIG. 9 is a view of a curbside bin.
FIG. 10 is a sectional view, taken along the plane X—X of FIG. 9.

A curbside bin 43 is now described with reference to FIGS. 9 and 10; said bin is suitable to receive the waste contained in the tray 13, shown in dot-and-dash lines in FIG. 9, in a position which is suitable for insertion in the bin 43 through the opening 44 provided with a door 45.

The partitions 46, 47, 48, 49 are provided inside said bin 43 and divide the space of the bin into compartments which extend from the bottom and end, in an upward region, at inlets which are arranged so that there is one inlet below each one of the compartments provided in the tray 13 when said is tray is fully inserted in the bin.

Thus, by removing the sliding bottom 20 of the tray 13 inserted in the bin 43, the glass 14a contained in the compartment 14 of the tray falls into the compartment delimited by the front wall 43a and the side wall 43b of the bin and by the partitions 46 and 49; the objects 15a made of metals other than aluminum contained in the compartment 15 of the tray fall into the compartment delimited by the front wall 43a of the bin and by the partitions 46, 49 and 47; the aluminum objects 16a contained in the compartment 16 of the tray fall into the compartment delimited by the front wall 43a of the bin and by the partitions 47, 49 and 48; the plastic objects 17a contained in the compartment 17 of the tray fall into the compartment delimited by the partition 48 and by the front wall 43a, the side wall 43c and the rear wall of the bin; and finally the paper 18a contained in the compartment 18 of the tray falls into the compartment delimited by the partitions 49 and 48 and by the side wall 43b and rear wall of the bin.

The result of the above is that inside the bin 43 the waste is collected so as to be sorted according to the same types isolated in the tray 13, and this condition is maintained in the many embodiments that are of course possible.

The bin 43 is provided with a bottom 50 which can open by sliding at right angles to the front wall 43a and is provided with a protrusion 51, with arms 52a and 52b which are rigidly coupled thereto, and with wheels 53 which are associated with the guides 54a and 54b which are rigidly coupled to the lower end of the side walls 43b, 43c of said bin, so as to allow complete opening of the bottom.

Anyhow the bottom of the bin can be openable in any manner.

Finally, the bin 43 is provided with rollers, as 55, for resting on the road paving, and with means for being gripped by a waste transport truck; said means are constituted by the recess 56 formed on the side wall 43c and by an identical recess formed on the wall 43b.

A truck 57 suitable to receive the waste contained in the bin 43 is now described with reference to FIGS. 11 to 14.

Figure 11:
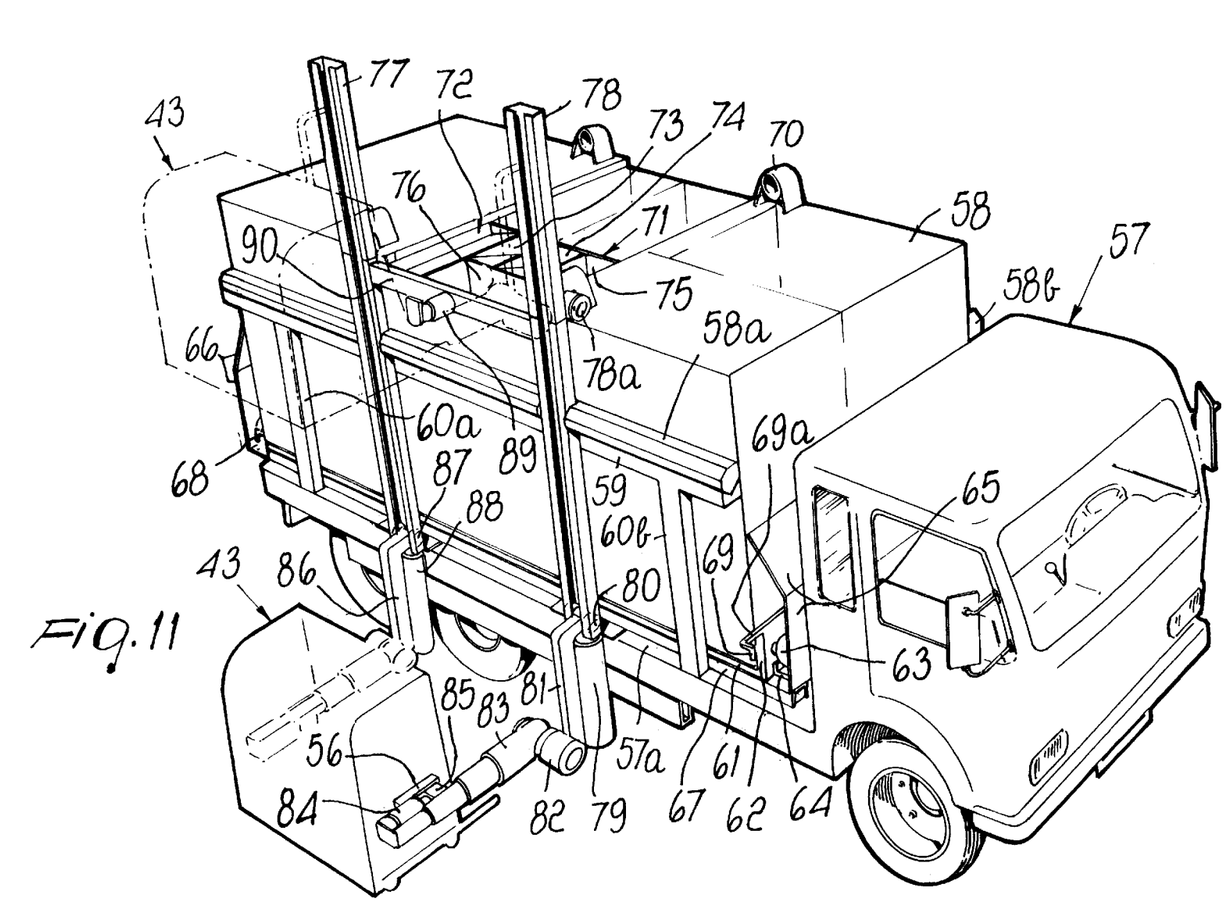
FIG. 11 is a view of a truck for transporting the waste from curbside bins to the final treatment plant.

Said truck first of all comprises the container 58, which is removable from the position shown in the figure so that it can be handled as required and is associated with the truck by virtue of the fact that the longitudinal brackets 58a, 58b with which it is provided rest on longitudinal members such as 59 which are supported by posts 60a and 60b which protrude from the platform 57a of the truck.

Said container is provided with a bottom 61 which can open by sliding transversely to the truck 57, and said bottom has, at the sides that lie parallel to the direction of motion, folds 62 provided with wheels 63 which are suitable to rest on guides 64 supported by the shaped plates 65, 66 which are rigidly coupled to the walls of the container 58 and are mutually connected by longitudinal members 67.

At the folds 62, the sliding bottom 61 is provided with means for engagement with handling means which comprise the pins 68 and 69, which protrude downward from brackets 69a which protrude with respect to said fold.

It should be readily observed that the above-described sliding bottom can be replaced with different openable bottoms.

On the lid of the container 58 there are engagement eyebolts 70 and there is an opening designated by the reference numeral 71.

Inside said container 58 walls suitable to divide the internal space into compartments are provided which extend from the bottom and end upward in the opening 71, at openings 72, 73, 74, 75, 76 which are arranged so that there is one opening below each one of the compartments provided in the bin 43 when said bin is arranged above said opening 71: in this way, the opening 72 lies below the compartment of the tray 43 that contains plastic objects; the opening 73 lies below the compartment of the bin that contains aluminum objects; the opening 74 lies below the compartment of the bin that contains objects made of metals except aluminum; the opening 75 lies below the compartment of the bin that contains glass; and finally the opening 76 lies below the compartment of the bin that contains paper.

It is immediately evident that when the waste contained in the bin 43 falls into the container 58 because the bottom has opened, the waste is divided, inside said container, according to type as it was in said bin 43 and earlier in the tray 13 of the compaction and disposal device.

The means for handling the bin 43 that equip the truck 57 are now described in detail.

Said means comprise the vertical guides 77 and 78, which rest on the platform 57a of the truck and have a portion which protrudes from the lid of the container which can be folded, in order to reduce the dimensions, by way of the action of hydraulic motors 78a for the guide 78.

The slider 80 slides inside the guide 78, by way of the action of the actuation cylinder 79 which is fixed to the structure of the truck 57; said slider is provided with the arm 81 for supporting the combined cylinder 82, which is capable of causing the rotation of the multistage actuation cylinder 83 between the horizontal working position shown in the figure and a vertical position in contact with the arm 81 so as to minimize space occupation, and is also capable of producing the horizontal translatory motion of said cylinder 83 in order to move it away from, or closer to, the bin 43.

The actuation cylinder 84 is provided at the end of the stem of the cylinder 83, acts in the opposite direction with respect to the cylinder 83 and has, at the end of its stem, the male element 85, which is suitable to enter the recess 56 provided on the side wall of the bin 43.

Similar means are supported by the arm 86 which is rigidly coupled to the slider 87, which can slide in the guide 77 by way of the action of the cylinder 88.

The truck 57 is also provided with means for handling the bottom 50 of the bin 43; said means comprise an abutment which is suitable to make contact with the protrusion 51 provided on said bottom, as will become apparent during the description of its operation; said abutment is constituted by the actuation cylinder 89, which is fixed to the longitudinal member 90 that connects the guides 77 and 78.

Before proceeding with the description of the operation of all that has been described above, it should be observed that the partitions inside the container and the means for handling the bin 43 and the bottom 50 of said bin can have any configuration.

The operation of the means for handling the bin 43 and the bottom 50 is now described starting from the situation shown in solid lines in FIG. 11, in which the bin 43 is still resting on the road paving but is already engaged by said handling means thanks to the insertion of the male element 85 in the recess 56 and of the corresponding male element in the corresponding opposite recess: this situation has been achieved through obvious maneuvers on the cylinders 82 and 83 and on the corresponding cylinders supported by the arm 86.

Figures 12, 13:
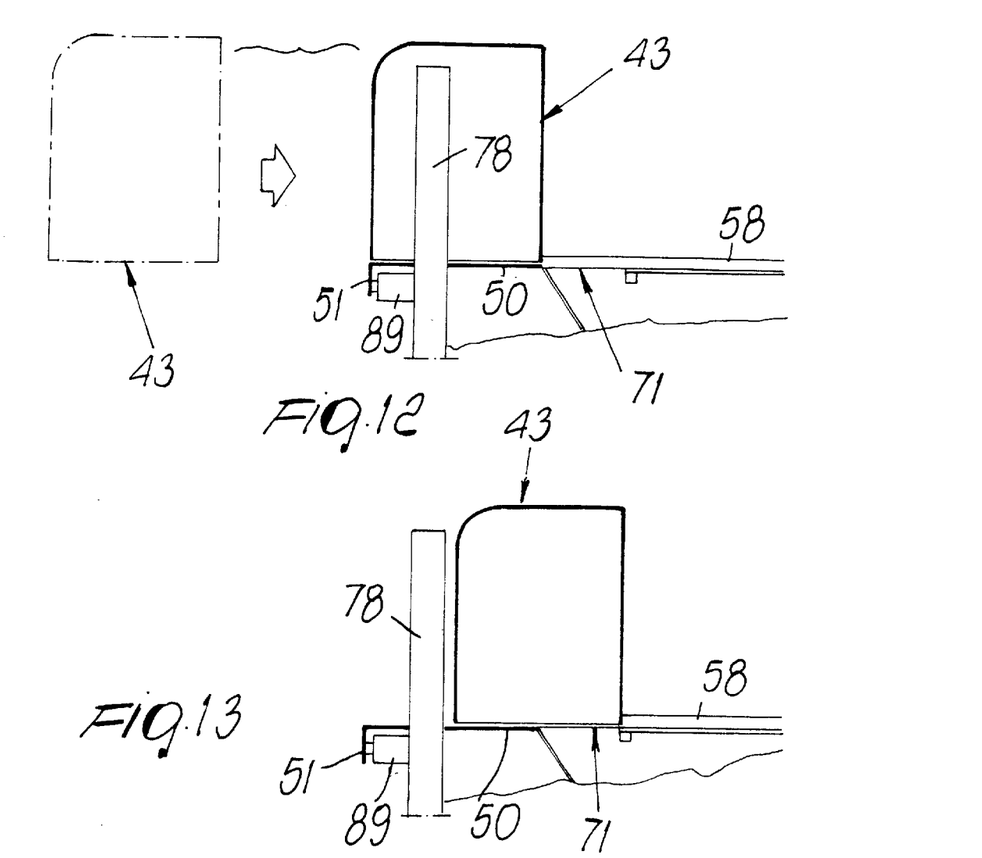
FIGS. 12, 13 and 14 are schematic views of different steps of the operation of the truck.
Figure 14:
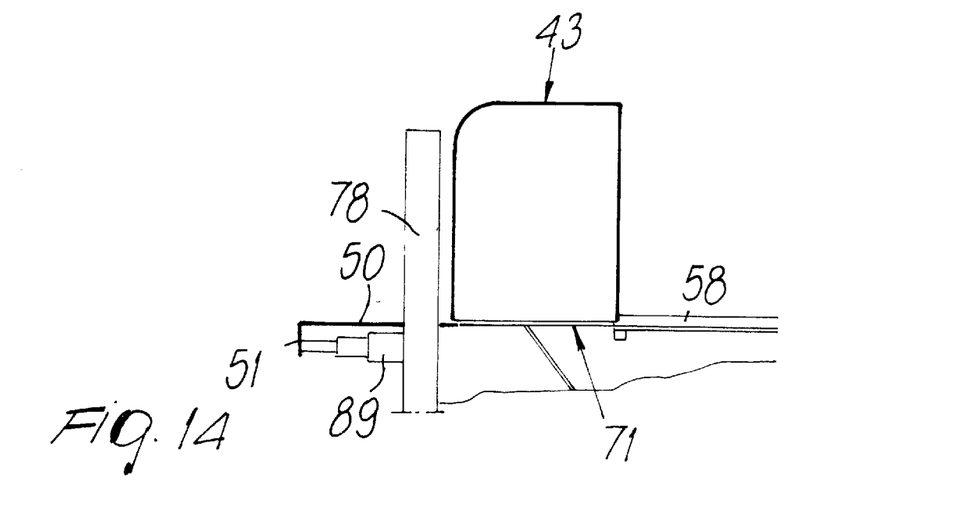

The sliders 80 and 87 begin to move upward, carrying the bin 43 to the position shown in dot-and-dash lines in FIGS. 11 and 12, directly above the lid of the container 58, and at this point the actuation cylinders 83 and 84 are activated together with the corresponding cylinders so as to produce the horizontal translatory motion, shown in FIGS. 12, 13 and 14, from the position shown in FIG. 12 in dot-and-dash lines to the position shown in solid lines in FIGS. 13 and 14.

Until the bin 43 reaches the position shown in solid lines in FIG. 12, the bottom 50 of said bin is not actuated in any way and thus remains closed, but in this position the protrusion 51 of said bottom makes contact with the abutment 89 and thus locks, sliding out with respect to the bin 43, which instead continues its stroke until it reaches the position shown in FIGS. 13 and 14, in which it perfectly overlaps the opening 71 provided in the lid of the container 58.

During the motion of the bin between the positions of FIGS. 12 and 13, which has occurred without activating the abutment actuation cylinder 89, the bottom has moved so as to allow the waste to fall into the openings 73, 74 and 75 and into the initial region of the opening 72.

In order to open the bottom completely, at this point the cylinder 89 is activated, as shown in FIG. 14, and the waste can thus also fall into the opening 76 and into the final region of the opening 72.

As mentioned earlier, the waste has been transferred from the bin 43 to the container 58 so as to keep it divided according to type, as it was in said bin 49 and earlier still in the tray 13 of the compaction and disposal device.

The plant for final waste treatment is now described with reference to FIGS. 15 and 16; said plant is suitable to receive said waste contained in the container 58, provided with a sliding bottom 61 and with an opening 71 in its lid, which is carried by the truck 57.

The container 58 is engaged by the carriage 91 of the bridge crane 92 by means of the insertion of the stems of the actuation cylinders of said carriage in the eyebolts such as 70 which are provided on the lid of the container, is raised from the position shown in dot-and-dash lines on the platform of the truck 57, and then lowered into the position shown in the figure, so that the longitudinal brackets 58a and 58b rest on the cross-members 93, 94 of the structure of the plant.

Figures 15, 16:
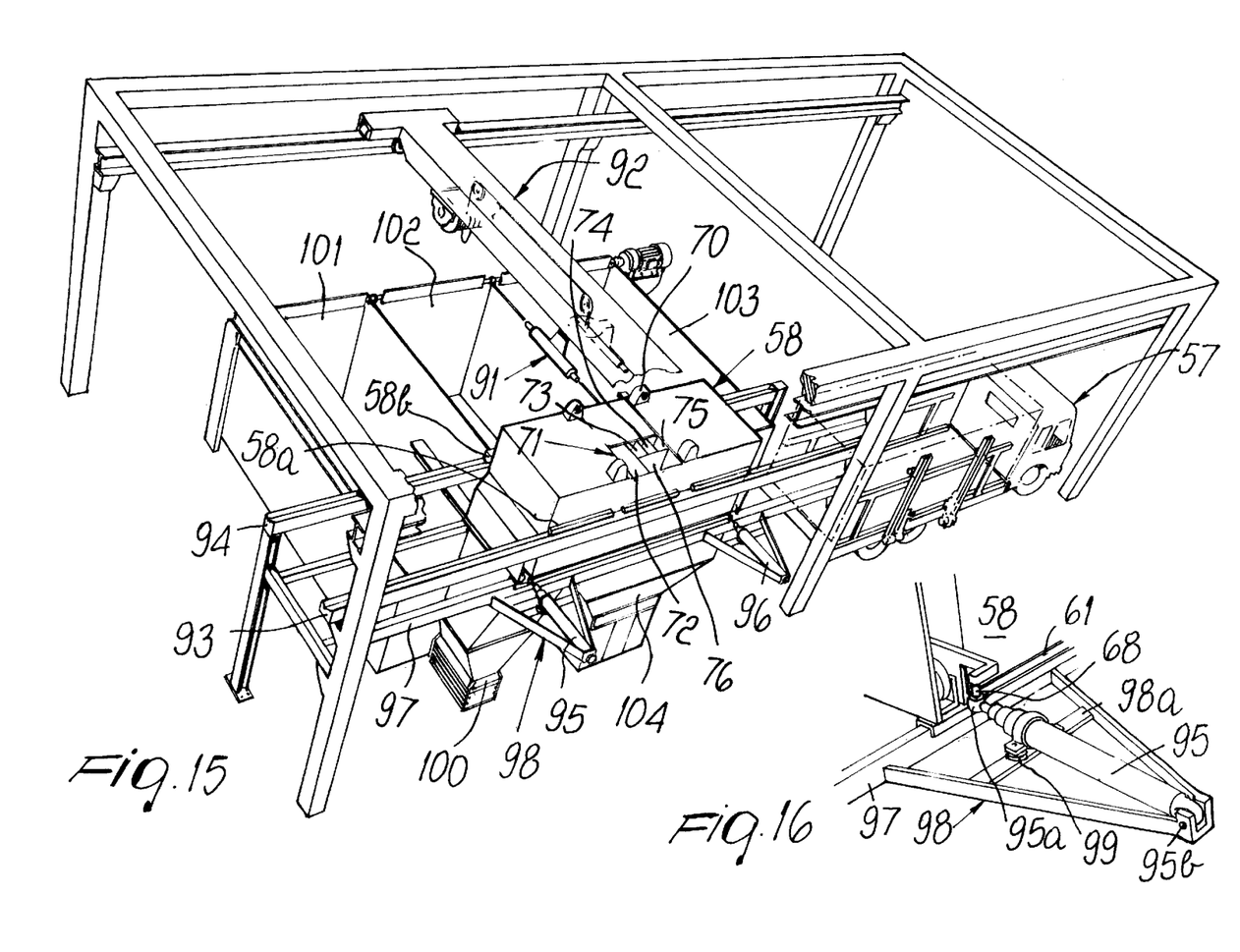
FIG. 15 is a view of the plant for the final treatment of the waste.
FIG. 16 is a view of a detail of FIG. 15.

During the final steps of the lowering of the container 58 toward the described position, the pins 68 and 69 that protrude from the folds of the sliding bottom 61 are inserted in eyelets which are provided at the end of the stems of the actuation cylinders 95 and 96, which are elastically supported by the longitudinal member 97, as shown by the detail of FIG. 16.

Said figure clearly shows the eyelet that is located at the end of the stem of the cylinder 95, is designated by the reference numeral 95a, and is crossed by the pin 68; and it can also be observed that said cylinder 95 is supported elastically, so as to facilitate the insertion of said pin in said eyelet, since it is pivoted at 95b to the bracket 98, which is fixed to the longitudinal member 97 and is rested on the cross-member 98a with an interposed spring such as 99.

In the final position shown in FIG. 15, the container 58 lies above inlets of channels, not shown in the figure, which convey the different types of waste received by gravity from the container to the various treatment points.

Said inlets are of course arranged so that there is one inlet below each one of the compartments provided in the container 58; therefore, below the compartment of the container that corresponds to the opening 72, which as mentioned contains plastic objects, there is provided the inlet of the channel that leads to the plastic press 100; below the compartment of the container that corresponds to the opening 73 and contains aluminum objects there is provided the inlet of the channel that leads to the container 101; below the compartment of the container that corresponds to the opening 74 and contains non-aluminum metallic objects there is provided the inlet of the channel that leads to the container 102; below the compartment of the container that corresponds to the opening 75 and contains glass objects there is provided the inlet of the channel that leads to the container 103; and finally, below the compartment of the container that corresponds to the opening 76 and contains paper there is provided the inlet of the channel that leads to the paper press 104.

The described plant, like all the above-described devices, is susceptible of numerous modifications and variations, all of which are within the scope of the inventive concept; all the details may further be replaced with other technically equivalent elements.

The disclosures in Italian Patent Application No. MN99A000020 from which this application claims priority are incorporated herein by reference.

What is claimed is:

1. A domestic waste treatment system, including a compaction and disposal device which comprises:
   a plurality of compaction chambers, for receiving different types of waste introduced through individual loading openings, said chambers being provided with at least one plate, and with actuation means for actuating said plate so as to act on said waste to reduce the volume thereof;
   at least one additional compartment for disposal of organic waste;
   a pull-out tray arranged below said compaction chambers and provided with partitions which form a plurality of compartments for receiving, by gravity, different types of waste contained at least in said compaction chambers and keeping the waste types separated, said tray being provided with an openable bottom and with guiding means;

a lid which is as sociable with the pull-out tray at said guiding means;

a pull-out divider which is arranged at the base of said plurality of compaction chambers.

2. The system of claim 1, wherein the loading inlets of the compaction chambers are located at the lid of the device.

3. The system of claim 1, wherein said actuation means for actuating the at least one plate comprise a hydraulic cylinder.

4. The system of claim 1, wherein said tray is provided with a tray bottom, openable by sliding, and with a tray lid which is movable by sliding motion.

5. The system of claim 3, wherein said compaction chambers are provided with a single plate adapted to process the waste contained in each one of said compaction chambers which are individually aligned.

6. The system of claim 5, wherein at least one of said compaction chambers is provided with a cutter having a blade and a contrast blade which are fixed respectively to said plate and to a wall of the compaction chamber that lies opposite said plate.

7. The system of claim 1, wherein the device comprises at least one chute connected to a loading opening, said loading opening being located at the lid of said device, and a further compartment, formed in said pull-out tray, for containing at least one type of waste which does not require compaction.

8. The system of claim 7, wherein said device further comprises at least one additional portion of space which is open exclusively at a loading and unloading opening.

9. The system of claim 8, wherein said compaction and disposal device is comprised within a basic module, said basis module being integratable in various ways, in order to provide different configurations of said device.

10. The system of claim 6, wherein said actuation means comprises said hydraulic cylinder for actuating the at least one plate and, operatively connected therewith, a drive provided with an electric pump.

11. The system of claim 6, wherein said actuation means comprises said hydraulic cylinder for actuating the at least one plate, and operatively connected therewith, a drive provided with a manual pump.

12. The system of claim 6, further comprising, in said compartment reserved for organic waste disposal which is included in the compaction and disposal device, a disposer which converts to pulp said waste introduced in the compartment by way of a loading opening located at the lid of said device.

13. The system of claim 12, further comprising a liquid pump and a reservoir contained in a structure which is removably contained in an additional module associated with the basic module of the device, said disposer being supplied with water drawn, by way of said liquid pump, from said reservoir.

14. The system of claim 12, wherein said disposer is contained in a compartment of the device and is supplied with water drawn from a tap located above said compartment.

15. The system of claim 13, further comprising a container accommodated in said structure, said disposer discharging pulp resulting from waste processing into said container which is removably mounted in said structure so as to be taken away for emptying.

16. The system of claim 13, further comprising a set of compaction means accommodated in said structure, said disposer discharging pulp resulting from waste processing into said set of compaction means.

17. The system of claim 13, wherein the disposer discharges pulp resulting from waste processing into a domestic sewage system.

18. The system of claim 12, wherein said compartment included in the compaction and disposal device for disposal of organic waste accommodates a container which is adapted to be periodically taken away for emptying.

19. A domestic waste treatment system according to claim 1, further comprising a curbside bin: which is suitable to receive said various types of waste contained in said pull-out tray provided with compartments to keep them separated, said bin comprising:

resting means for resting on a road paving;

gripping means for engagement by a waste transport truck;

an openable bottom;

an opening provided in a wall, at an elevated position, proximate to a lid, so as to allow complete insertion of said tray in said bin;

a plurality of walls for dividing an internal space at the bin into compartments which extend from bottom and end upward at openings which are arranged so that there is one opening below each one of the compartments provided In said tray, when said tray is fully inserted in the bin.

20. The system of claim 19, comprising an openable bottom which can open by sliding.

21. The system of claim 20, wherein said openable bottom that can open by sliding is provided with a protrusion at its lower surface.

22. The system of claim 19, wherein said gripping means for engagement by a truck comprise two recesses formed on opposite walls of the bin.

23. A domestic waste treatment system according to claim 19, further comprising a container which is removably mounted on a truck, said container being provided with an opening formed in a lid thereof and with a plurality of walls which are adapted to divide an internal space thereof into compartments which extend from the bottom of said internal space and end upward, in said opening, at 3 plurality of smaller openings which are arranged so that there is one smaller opening below each one of said compartments provided in said bin, when said bin is located above said opening, said container being provided with an openable bottom.

24. The system of claim 23, comprising said truck which is adapted to receive the waste contained in a bin provided with an openable bottom, wherein said bin handling means are provided so as to pick up said bin from the position in which it rests on the road paving and to move the bin, first in a substantially vertical direction, up to a level that lies above the lid of the container, and then in a substantially horizontal direction to a position above the opening provided within said lid, whereupon said bottom handling means being operatable for handling the openable bottom of the bin.

25. The system of claim 24, comprising the truck for receiving the waste contained in the bin, said bin being provided with the openable bottom and with engagement recesses formed on mutually opposite sides thereof, wherein said bin handling means comprise: two vertical guides which protrude from a platform of the truck; a slider being slidable in each one of said guides; movement means for moving said slider, said slider having an arm supporting a first combined rotary pusher cylinder and a second actuation cylinder said first pusher cylinder producing rotation of said second actuation cylinder between a vertical position for minimum space occupation in contact with said vertical guides and a horizontal active position, and a horizontal translatory motion of said second actuation cylinder in a direction which is parallel to the plane that contains said vertical guides; a third actuation cylinder being provided at the end of a stem of said second cylinder, said third cylinder acting in the opposite direction with respect to said second cylinder and having, at the end of a stem thereof, a male element which is adapted to enter said recesses provided on the sides of the bin.

26. The system of claim 25, including the truck for receiving the waste contained in the bin provided with the bottom is openable by sliding, said bin being provided with a protrusion at the lower surface, comprises said bin handling means for picking up said bin from the position in which it rests on the road paving and to move the bin, first in a substantially vertical direction up to a level that lies directly above the lid of the container, and then in a substantially horizontal direction up to the position that lies above the opening formed within said lid, and further comprises said bottom handling means for handling the bottom of the bin which is openable by sliding, said bottom handling means comprising an abutment which is adapted to make contact, at an appropriate time, with the protrusion provided at the lower surface of said bottom during the motion of the bin in a substantially horizontal direction.

27. The system of claim 26, wherein said abutment adapted to make contact with the protrusion of the bottom, comprises a monolithic block.

28. The system of claim 26, wherein said abutment adapted to make contact with the protrusion of the bottom, comprises an actuation cylinder.

29. The system of claim 26, wherein said removable container comprises, at the sides thereof, longitudinal brackets, resting on longitudinal members supported by posts, said posts rising from the platform of the truck.

30. The system of claim 29, wherein the bottom of the container, which is openable by sliding, comprises, at the sides that are parallel to an opening direction thereof, folds provided with wheels, said wheels resting on guides located at the walls of the container, and with engagement means for engaging handling means.

31. The system of claim 30, wherein said engagement means provided on said folds of the sliding bottom of the container comprise, for each fold, a pin protruding vertically downward from a bracket of said respect fold.

* * * * *